United States Patent
Chen et al.

(10) Patent No.: US 11,209,329 B2
(45) Date of Patent: Dec. 28, 2021

(54) LIQUID ENCAPSULATION DEVICE AND METHOD FOR FABRICATING THE SAME

(71) Applicant: The Chinese University of Hong Kong, Hong Kong (CN)

(72) Inventors: Shih-Chi Chen, Hong Kong (CN); Xiangyu Fan, Hong Kong (CN); Ni Zhao, Hong Kong (CN); Yan Huang, Hong Kong (CN); Ningqi Luo, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 497 days.

(21) Appl. No.: 15/879,964

(22) Filed: Jan. 25, 2018

(65) Prior Publication Data

US 2019/0226931 A1  Jul. 25, 2019

(51) Int. Cl.
*G01L 7/18* (2006.01)
*G01D 11/24* (2006.01)
*A61B 5/00* (2006.01)
*A61B 5/021* (2006.01)

(52) U.S. Cl.
CPC .......... *G01L 7/182* (2013.01); *A61B 5/02108* (2013.01); *A61B 5/681* (2013.01); *G01D 11/245* (2013.01)

(58) Field of Classification Search
CPC ..... G01L 7/182; A61B 5/02108; A61B 5/681; G01D 11/245
See application file for complete search history.

(56) References Cited

U.S. PATENT DOCUMENTS

| 4,691,794 A * | 9/1987 | Larsen ................. G01G 3/1402 177/211 |
| 4,738,267 A * | 4/1988 | Lazorthes ............. G01L 9/0051 600/561 |
| 8,991,265 B2 * | 3/2015 | Dekker ................. G01L 19/148 73/862.045 |

* cited by examiner

*Primary Examiner* — Nathaniel T Woodward
(74) *Attorney, Agent, or Firm* — Saliwanchik, Lloyd & Eisenschenk

(57) ABSTRACT

A liquid encapsulation device for embedding sensor is provided. The liquid encapsulation device comprises a substrate having an upper surface with a central concave portion; at least one protection layer sealed on the upper surface of the substrate; and at least one sensor fixed on the protection layer. Wherein, the central concave portion is filled with liquid and the sensor is arranged above the central concave portion.

8 Claims, 7 Drawing Sheets

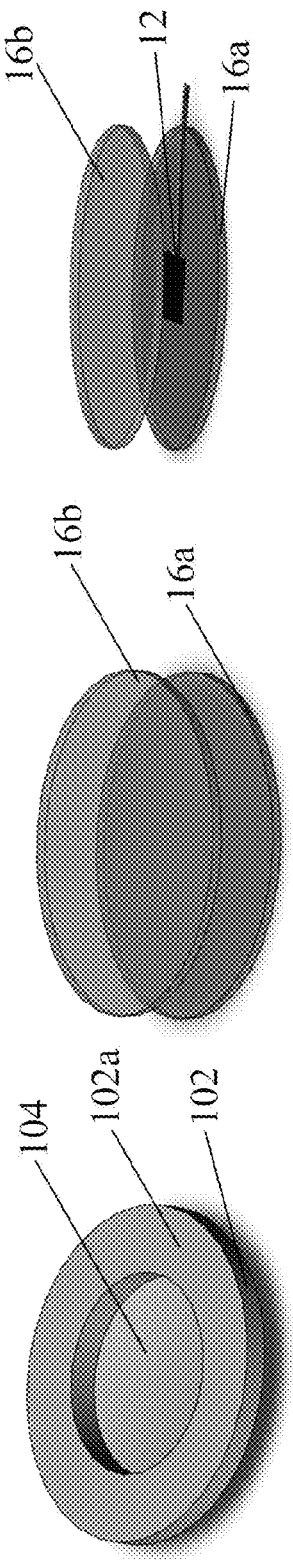
Fig. 2A
Fig. 2B
Fig. 2C
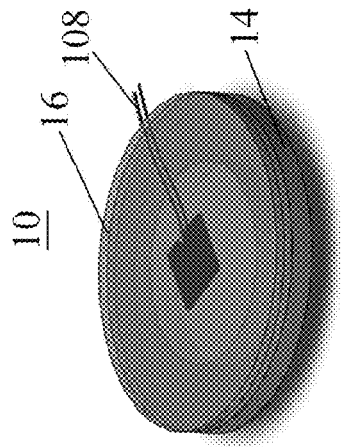
Fig. 2D
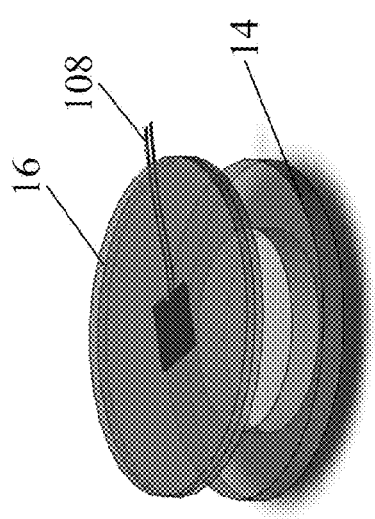
Fig. 2E
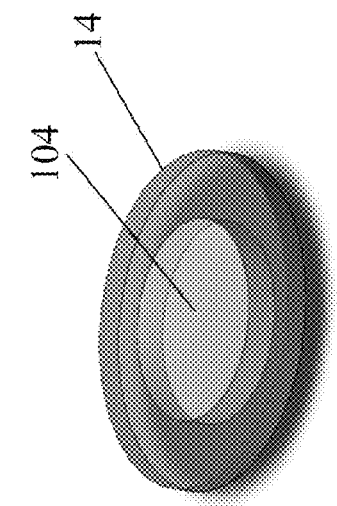
Fig. 2F

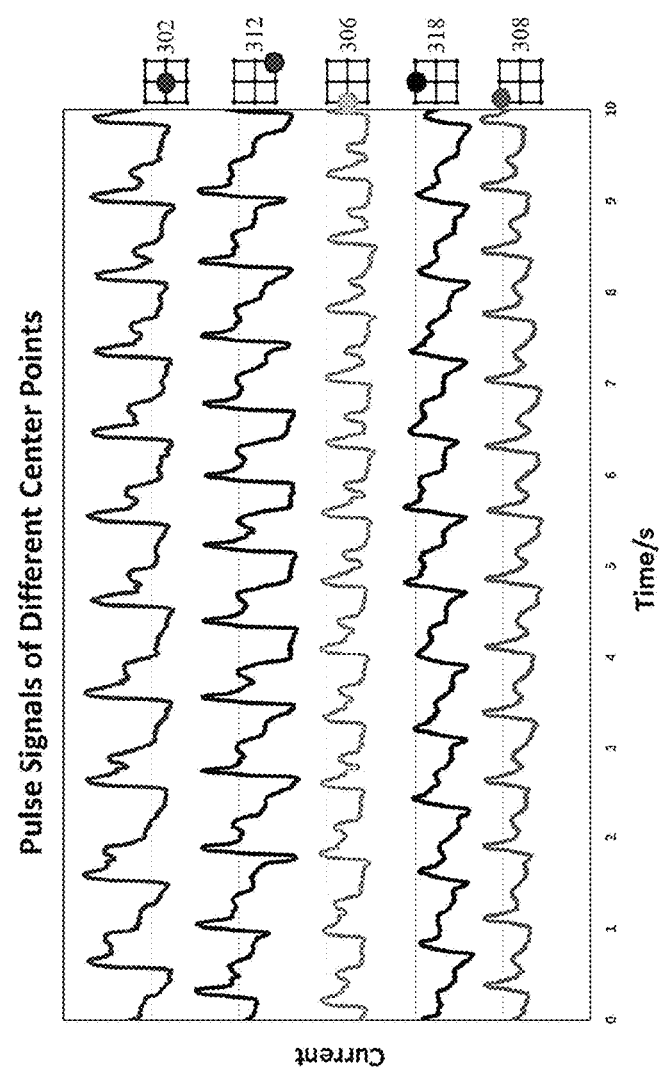
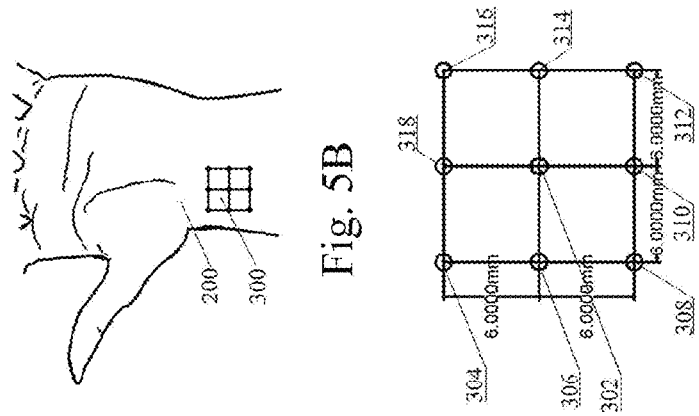
Fig. 5B
Fig. 5C
Fig. 5A

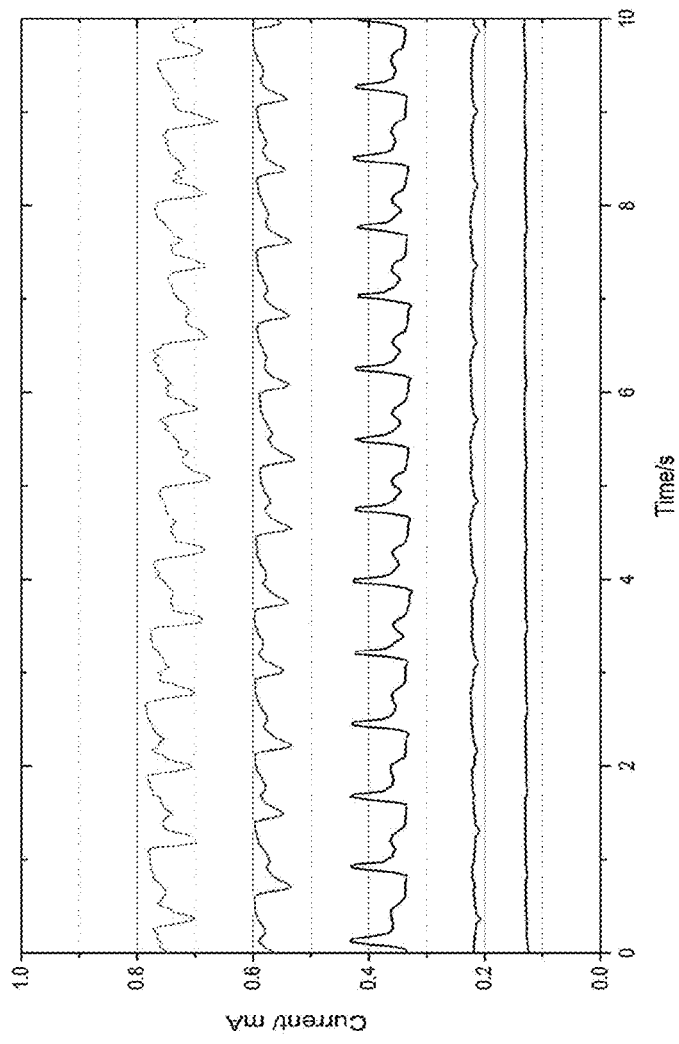
Fig. 6A
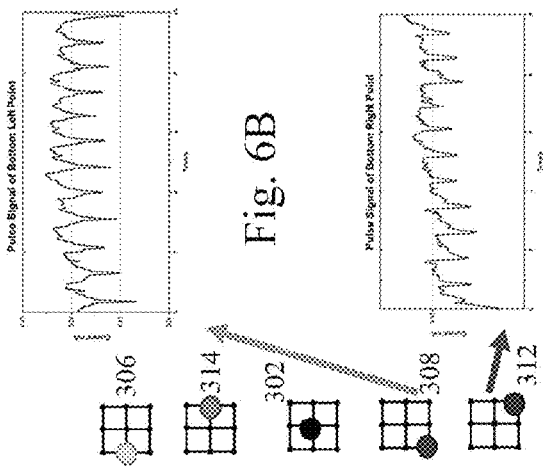
Fig. 6B
Fig. 6C

LIQUID ENCAPSULATION DEVICE AND METHOD FOR FABRICATING THE SAME

TECHNICAL FIELD

The present disclosure generally relates to a liquid encapsulation device, more particularly, to a liquid encapsulation device for flexible sensors. The present disclosure further relates to a method for fabricating the liquid encapsulation device. In addition, the present disclosure also relates to a wearable device comprising the above liquid encapsulation device.

BACKGROUND

It is well known that Blood Pressure (BP) is a critical physical parameter that gives direct indication to many diseases, e.g., cardiovascular diseases. A challenge for measuring the BP is how to obtain BP data continuously and precisely based on small-scale cuffless electronic devices.

Current BP measurement devices are mostly cuff-based. They are bulky and uncomfortable to wear, and only capable of performing snapshot measurements. Besides, the power consumption of these devices is high, for example, a typical automatic wrist BP monitor (Omron HEM-642-HK, 3 V, and 2.5 W) operates on two AA batteries and can only last for several hours.

Another method for measuring BP is Photoplethysmography (PPG). PPG is a non-invasive, low-cost technique to acquire blood volume pulse by optical means, and can be used, typically in combination with electrocardiogram (ECG) sensors, to measure BP. A PPG sensor includes at least one light-emitting diode (LED) as the light source to illuminate the skin and a photodetector to measure the intensity variation of reflected or transmitted light. Since a typical PPG sensor have a power consumption of 10 mW~100 mW, frequent replacement of batteries for continuous BP monitoring becomes inevitable.

When used for pulse tracking or BP monitoring, bare pressure sensors are extremely sensitive to misalignment, i.e., signals of pressure sensors distort severely when misaligned with the artery under the skin for more than 1 mm. With the poor signal quality, pulse transit time (PTT) cannot be precisely estimated as the characteristic point of the pulse wave becomes vague and ambiguous, which results in errors when estimating the BP.

Thus, the development of new portable/wearable pressure sensors with clinically required precision for continuously monitoring of BP in an unobtrusive way is critically important. One critical issue for such wearable devices is that the sensor only works when it is precisely aligned with the arteries under the skin (±0.25 mm) with appropriate pre-loads, which make it difficult implement without specialized tools and assistance from professional staff.

Existing commercially available wearable devices are mostly fitness trackers, which provide recordings on heart rate, sleep behavior, and step count. There is no similar products or technologies that can enhance the performance of all small-scale wearable/flexible devices, e.g., pulse tracker or BP sensor, i.e., to relax the precision alignment requirement.

Therefore, there is a need for a technology that can substantially relax the alignment precision without sacrificing the signal quality.

SUMMARY

In current technology-intensive and high product margin market, more and more attention focuses on high-precision wearable BP monitoring devices. It is found that the capsule technology can substantially boost the performance of these products. The present disclosure provides a liquid encapsulation device which can substantially relax the required alignment precision between the sensor and the target, e.g., blood vessels, and can achieve high robustness and enhanced mechanical properties. The present disclosure also addresses critical issues for wearable electronics/devices to obtain stable and reliable signal from the body.

The liquid encapsulation device with integrated BP sensor described in this disclosure presents high quality, high precision, medical grade results, which have great potential of commercialization. Undistorted pulse signals collected with ±6 mm sensor misalignment demonstrate great potential of personal BP measurement and ease of installation. Compared with PPG sensor that contains LED as light sources, the liquid encapsulation sensor requires much less power consumption (<10 nW), which enables long-term BP monitoring. The liquid encapsulation sensor presents a promising solution to make BP meter truly wearable.

The capsule technology has great market potential and is compatible with all small-scale flexible or wearable sensors, e.g., pressure sensors, strain sensor, displacement sensor, or vibration sensor. The liquid encapsulation device may generate important impact on the health care industry, i.e., enhancing the performance of wearable devices, and improve the life of the elderly or people with cardiovascular diseases.

According to an aspect of the present disclosure, a liquid encapsulation device may comprise a substrate having an upper surface with a central concave portion; at least one protection layer sealed on the upper surface of the substrate; and at least one sensor fixed on the protection layer at a side faced the substrate. The central concave portion may be filled with liquid and the sensor may be arranged above the central concave portion. According to an embodiment of the disclosure, the device may comprise at least two protection layers sealed on the upper surface of the substrate. The sensor may be fixed between the at least two protection layers.

According to an embodiment of the disclosure, the liquid encapsulation device may further comprise an adhesive layer for curing the protection layers onto the upper surface of the substrate. The adhesive layer may be made of but not limited to uncured silicones, e.g., Ecoflex 00-30 (Silicone) or PDMS.

According to another aspect of the present disclosure, a method for fabricating a liquid encapsulation device may comprises casting a substrate having an upper surface with a central concave portion; fixing at least one sensor on a protection layer at a side faced the substrate; injecting liquid into the central concave portion of the substrate such that the sensor is arranged above the central concave portion; and sealing the protection layers with the substrate.

According to an embodiment of the disclosure, the method may further comprise fixing the sensor between at least two protection layers; and sealing the at least two protection layers on the upper surface of the substrate.

According to an embodiment of the disclosure, the method may further comprise pouring uncured silicone into a mold and degassing the uncured silicone for 40 minutes; and disposing the mold with the uncured silicone into an oven at 80° C. for 60 mins.

According to an embodiment of the disclosure, wherein the sealing may further comprise applying uncured silicone to the substrate and the protection layers; and curing the uncured silicone at 80° C. for 60 mins.

According to an embodiment of the disclosure, the injected liquid for example can be any one of glycerol and water and the like.

According to an embodiment of the disclosure, for example, the sensor may be selected from a group consisting of pressure sensor, strain sensor displacement sensor, vibration sensor and any other suitable sensor.

According to an embodiment of the disclosure, the substrate and the protection layers may be made of same or different stretchable materials, for example, silicone, i.e., Eco-flex, PDMS, and rubber etc.

According to another aspect of the present disclosure, a wearable device comprising the above liquid encapsulation device is provided. The liquid encapsulation device can be implementing on a watch, a wrist band, a head band, glasses, ear sets and the like.

BRIEF DESCRIPTION OF THE DRAWING

Exemplary non-limiting embodiments of the present disclosure are described below with reference to the attached drawings. The drawings are illustrative and generally not to an exact scale. The same or similar elements on different Figs. are referenced with the same reference numbers.

FIGS. 2A-F shows an exemplary process for fabricating the liquid encapsulation device according to an embodiment of the present disclosure;

FIG. 5A shows signals recorded by the liquid encapsulation device at five arbitrarily selected points on the grid with a size of 12×12 mm$^2$, wherein corresponding pressure data is labeled with a dot in a 9-point grid to indicate the measuring location; FIG. 5B show the BP measurement points on wrist; and FIG. 5C shows a dimension of the 9-point grid;

FIG. 6A shows signals recorded by the bare BP sensor at five arbitrarily selected points on the grid with a size of 12×12 mm2, wherein corresponding pressure data is labeled with a dot in a 9-point grid to indicate the measuring location;

FIG. 6B and FIG. 6C shows scaled-up signals of the bottom left point and the bottom right point;

DETAILED DESCRIPTION

Reference will now be made in detail to some specific embodiments of the disclosure including the preferable modes contemplated by the inventors for carrying out the disclosure. Examples of these specific embodiments are illustrated in the accompanying drawings. While the disclosure is described in conjunction with these specific embodiments, it will be understood that it is not intended to limit the disclosure to the described embodiments. On the contrary, it is intended to cover alternatives, modifications, and equivalents as may be included within the spirit and scope of the disclosure as defined by the appended claims. In the following description, numerous specific details are set forth in order to provide a thorough understanding of the present disclosure. The present disclosure may be practiced without some or all of these specific details. In other instances, well-known process operations have not been described in detail in order not to unnecessarily obscure the present disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1A:
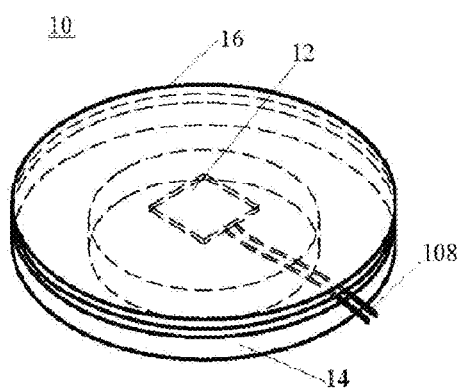
FIG. 1A shows an example of the liquid encapsulation device according to an embodiment of the present disclosure, where a sensor is embedded in a liquid capsule.
Figure 1B:
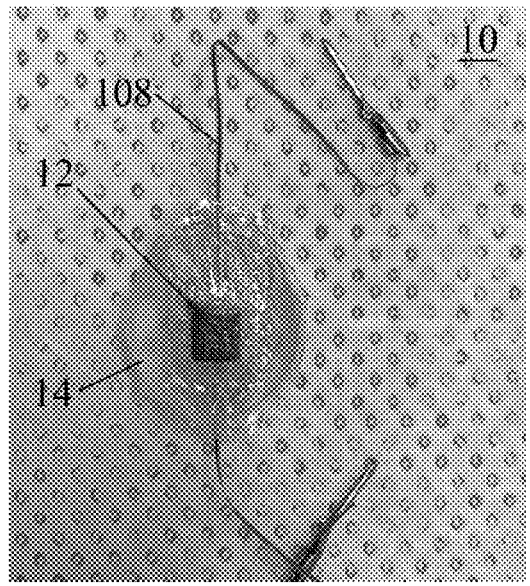
FIG. 1B shows a photograph of the liquid encapsulation device according to an embodiment of the present disclosure.

FIG. 1A shows an example of the liquid encapsulation device 10 according to an embodiment of the present disclosure, where a sensor 12 is embedded in a liquid encapsulation element 14 for measuring the epidermal pulses as well as blood pressure (BP). FIG. 1B shows a photograph of the liquid encapsulation device 10 with a sensor 12 embedded. It should be noted that the pressure sensor is only an example and any kind of sensors, such as strain sensor, displacement sensor, and vibration sensor etc. can also be embedded in the liquid encapsulation element 14.

Figure 1C:
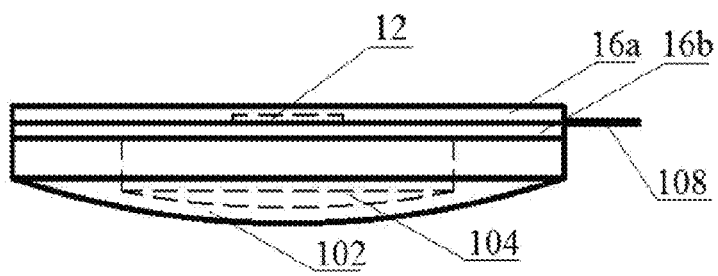
FIG. 1C shows a cross-section view of the liquid encapsulation device according to an embodiment of the present disclosure.

FIG. 1C shows a cross-section view of the liquid encapsulation device 10 according to an embodiment of the present disclosure. As shown in FIG. 1C, the liquid encapsulation device 10 may comprise a substrate 102 having an upper surface 102a (shown in FIG. 2A) with a central concave portion 104; at least one protection layers 16 sealed on the upper surface 102a of the substrate 102; and at least one sensor 12 fixed on the protection layer 16 at a side faced the substrate 102. Usually, the central concave portion 104 is filled with liquid and the sensor 12 is arranged right above the central concave portion 104.

In a preferable embodiment, the liquid encapsulation device 10 can comprise at least two protection layers 16a and 16b sealed on the upper surface 102a of the substrate 102. The sensor 12 can be fixed between the two protection layers 16a and 16b.

In an exemplary embodiment of the present disclosure, the sensor, for example, may be any of pressure sensor and strain sensor and the like. It should be noted that the pressure sensor and strain sensor are only example rather than limitation. The liquid encapsulation device 10 can embed various types of small-scale flexible or rigid sensors or electronic devices to enhance their performance, including relaxing the alignment requirement between the sensor/devices and the target, e.g., blood vessels; filtering out redundant motion artifacts and high-frequency noises; and improving the sensitivity and conformability of the embedded devices. The liquid encapsulation device 10 can be designed into any suitable dimension to hold different small-scale sensing element, such as pressure sensor and strain sensor or other electronic devices.

The liquid injected into the liquid encapsulation 14 can be any fluid that remains its fluid form at room temperature. The fluid in the encapsulation 14 serves as a medium to propagate the pressure wave from the target, e.g., epidermal pulses from blood vessels, when measuring heart beats and pulse signals from the blood vessels.

The liquid encapsulation device 10 can further comprises an adhesive layer for curing the protection layers onto the upper surface of the substrate. For example, the adhesive layer can be made of uncured silicone.

FIGS. 2A-2F show an exemplary process for fabricating the liquid encapsulation device 10 according to an embodiment of the present disclosure. The method can comprise the following steps:

(a) casting a substrate 102 having an upper surface 102a with a central concave portion 104;

(b) casting at least one protection layer 16;

(c) fixing at least one sensor 12 on the protection layer 16 at a side faced the substrate 102;

(d) injecting liquid into the central concave portion 104 of the substrate 102 such that the sensor 12 is arranged right above the central concave portion 104; and (e) sealing the protection layers 16 with the substrate 102.

In a preferable embodiment, the method can further comprise casting at least one protection layers 16a and 16b and fixing the at least one sensor 12 between the two protection layers 16a and 16b.

As described above, the embedded sensor 12 can be any small-scale sensors, e.g., pressure sensor, strain sensor, displacement sensor, or vibration sensor. The cast layer substrate 102 and the protection layers 16a and 16b can be made of silicone (e.g., Eco-flex, PDMS or any stretchable materials). Sealing the layers can be achieved by applying uncured liquids, e.g., silicone, to the cured silicone layers, followed by standard curing process with appropriate external pressure. In principle, the material of the capsule should be soft and stretchable to maximize the sensitivity of the embedded sensor. If the capsule shell is too stiff, the signal will be degraded or de-amplified. Accordingly, Eco-flex or PDMS are (but not limited to) good candidates for as the capsule. To fabricate a capsule, the uncured silicone is poured into pre-fabricated molds. Before curing, the liquid silicone needs to be degassed for 40 minutes. Next, the mold containing liquid silicone may be kept in an oven at 80° C. for 60 minutes to curing. Following this process, the substrate 102 and the two protective layers 16a and 16b are fabricated. In order to sandwich a sensor 12 between the two protective layers 16a and 16b, one first place the sensor 12 between the two protective layers 16a and 16b, followed by bonding via liquid silicone. After the sensor being embedded and sealed between the two protective layers 16a and 16b, liquids, for example but not limited to, glycerol or water, are injected into the bottom substrate. Next, a new layer of uncured silicone is applied to the substrate 102. Lastly, the integrated protective layer embedded the sensor 12 is placed upon the substrate 102 (filled with liquid), followed by a final curing step (80° C. for 60 minutes) to seal the liquid and completes the capsule fabrication process.

It should be understood that the liquid encapsulation device 10 fabricated with the above method can be integrated in any appropriate wearable device, such as watch, wrist band, head band, glasses, ear set and the like. When integrating the liquid encapsulation device 10 in the wearable device, a proper pre-load can be applied.

Figure 3A:
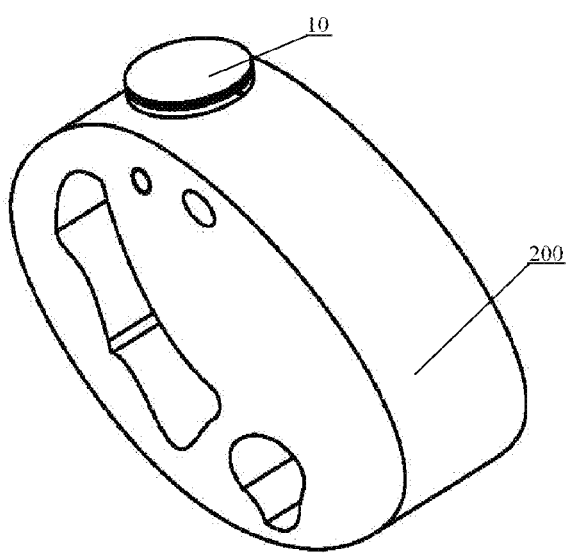
FIG. 3A shows a cross-section view of a wrist with a liquid encapsulation device applied according to an embodiment of the present disclosure.
Figure 3B:
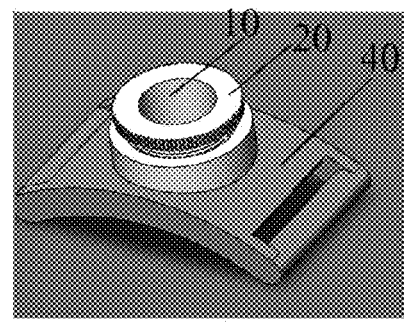
FIG. 3B shows a CAD model of a capsule holder for receiving the liquid encapsulation device according to an embodiment of the present disclosure.
Figure 3C:
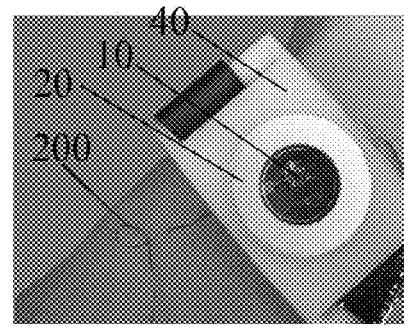
FIG. 3C shows a prototype liquid encapsulation device/model worn on a person wrist for heart beat and BP measurement according to an embodiment of the present disclosure.

As illustrated in FIGS. 3A-3C, the liquid encapsulation device 10 is attached to a person's wrist 200 with appropriate preload via a sensor holder 20 and a wristband 40. FIG. 3A shows a cross-section view of a wrist 200 with a liquid encapsulation device 10 applied according to an embodiment of the present disclosure. FIG. 3B shows a CAD model of a capsule holder 20 for receiving the liquid encapsulation device 10. This liquid encapsulation device 10 can obtain energy from the contact area, where the radial artery lies under the nearby skin. In each heart beat cycle, blood flows through the radial artery and imposes a pressure to the artery. This quasi-periodic pressure induces a stress wave propagating through subcutaneous tissues and reaching to the skin above the artery. This generates a pressure wave in the encapsulated liquid 10 and lastly to the embedded sensor 12. Accordingly, the liquid encapsulation 14 effectively broadens the sensor's detection area, making it equivalent to the size of the liquid encapsulation 14.

In an exemplary embodiment, a carbon black-decorated fabric BP sensor is used to demonstrate the performance enhancement of the liquid encapsulation device.

Figure 4A:
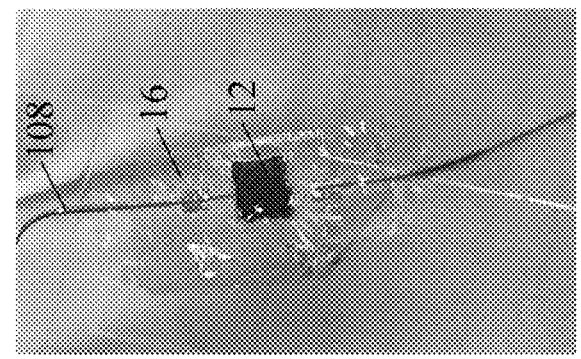
FIG. 4A shows an exploded view of a flexible pressure sensor embedded in the liquid encapsulation device according to an embodiment of the present disclosure.
Figure 4B:
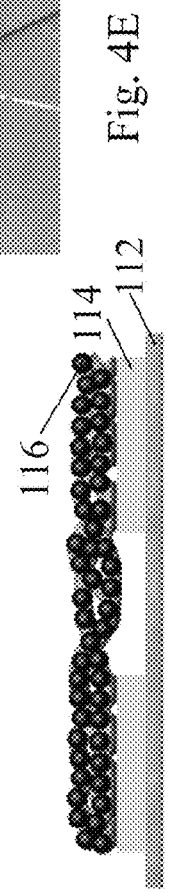
FIG. 4B shows a schematic view of a flexible pressure sensor embedded in the liquid encapsulation device according to an embodiment of the present disclosure.

FIGS. 4A-4E show the overall structure of the flexible carbon black-decorated fabric BP sensor 12. As shown in FIG. 4A shows the flexible carbon black-decorated fabric BP sensor 12 may comprise a polyimide (PI) substrate 112, a interdigital electrode 114 provided on the PI substrate 112, a carbon black-decorated fabric 116 lies on the interdigital electrode 114 and the PI substrate 112, and a Polyethylene Naphthalate (PEN) encapsulation 118 covering the PI substrate 112 together with the interdigital electrode 114 and the carbon black-decorated fabric 116. As shown in FIG. 4B, the sensor can be well flexible.

Figure 4C:
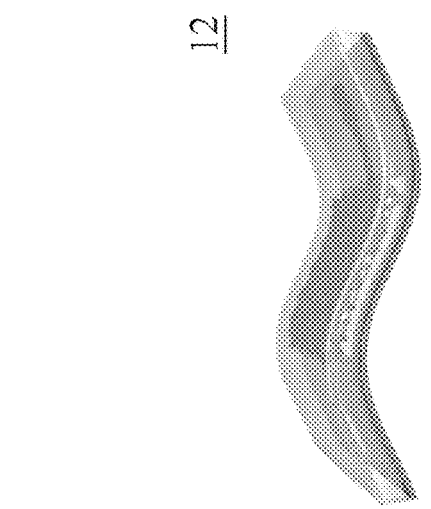
FIG. 4C shows a material deformation of the flexible pressure sensor without pressure according to an embodiment of the present disclosure.
Figure 4D:
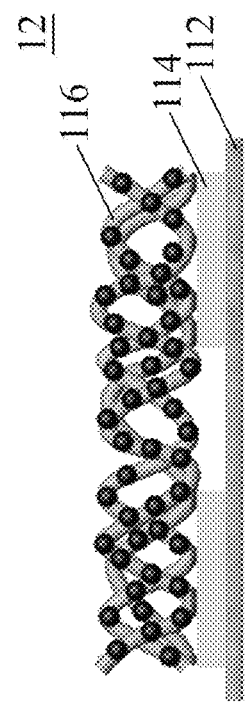
FIG. 4D shows a material deformation of the flexible pressure sensor under pressure according to an embodiment of the present disclosure.
Figure 4E:
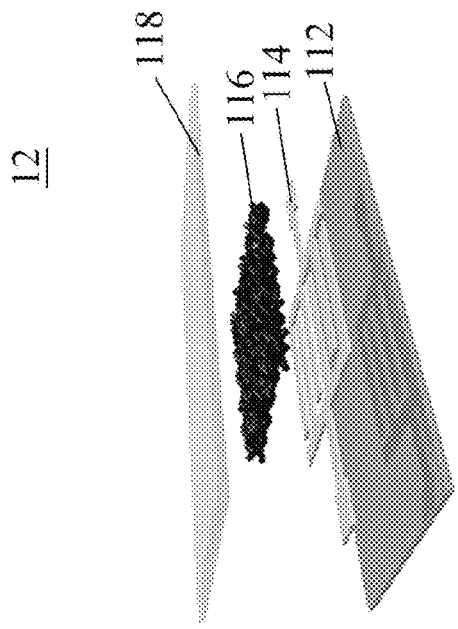
FIG. 4E shows a photograph of the flexible pressure sensor embedded in the liquid encapsulation device according to an embodiment of the present disclosure.

When pressure is applied to the BP sensor 12, both the contact points among the carbon particles and the contact points at the carbon/Au interface increase (FIG. 4D). The total contact points reduce when the pressure decreases (FIG. 4C). Experimental results show that the sensor 12 exhibits good linearity within 0 to 35 kPa with very little hysteresis.

Next, in order to demonstrate that the BP sensor embedded in the capsule is insensitive to misalignment, some experiments for measuring the pulse wave of the wrist are performed.

In the experiments, a source meter is used to measure the current going through the sensor. Since the sensor can be precisely calibrated, the measured currents can be used to directly report the pressure wave. To demonstrate the misalignment relaxation capability of the capsule technology, the sensor readings from different selected locations 300 (i.e., a nine point grid, where the center point refers to the aligned position) on the wrist 200 as shown in FIGS. 5A-5C is purposely compared. The selected locations 300 cover an area of 12×12 mm².

FIGS. 5A-5C and FIGS. 6A-6C present the measured pressure data from the capsule BP sensor and bare BP sensor respectively. From FIGS. 5A-5C, it can be observed that the liquid encapsulation sensor 12 always records high-quality signals without distortion even the liquid encapsulation sensor is misplaced by as far as ±6 mm. In all measured points (for example, locations 302, 312, 306, 318, and 308 shown in FIGS. 5A-5C), the characteristic point of the pulse wave can be clearly identified. Contrarily, as shown in FIGS. 6A-6C, it can be observed that although the BP sensor collects great signals at the center point 302 of the square grid 300, the pressure signals quickly deteriorate and become severely distorted as the sensor moves to other points (for example, points 308, 312) on the grid 300.

In addition, in order to show the capsule-embedded sensor still preserves the good characteristics of the original pressure sensor, another experiment is preformed. In this experiment, the performance of the BP sensor with/without the liquid encapsulation is tested and compared when the loads are directly applied to the center of the sensor. The sensitivity, linearity, hysteresis, and stability of the sensors are characterized in the experiment. In general, BP sensors need high sensitivity to capture the weak epidermal pulses; good linearity within at least 15 kPa; small hysteresis to ensure the detected signals are not distorted; and good stability over long-term use.

Figure 7A:
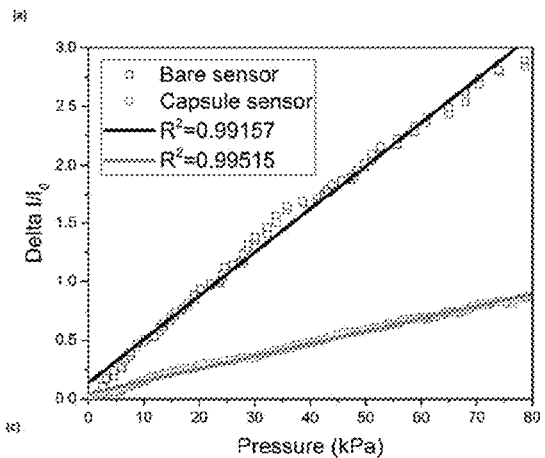
FIG. 7A shows sensitivity and linearity characterization of the BP sensor with/without capsules.

When a voltage is applied to a sensor, the sensitivity is defined as $$S = \frac{\Delta I / \Delta I_0}{\Delta P},$$

where $\Delta I$ is the current change in response to the pressure change $\Delta P$ and $I_0$ is the zero-load current. The sensitivity and linearity characterization of the sensors with/without the liquid encapsulation are shown in FIG. 7A. Note that the pressure is found by dividing the loading force by the sensor area. For the liquid encapsulation sensor, the force is applied to the substrate of the capsule. So, the calculated pressure at the embedded sensor is lower than the one measured without the liquid encapsulation, leading to slightly reduced sensitivity. Both sensors have a wide linear range.

Figure 7B:
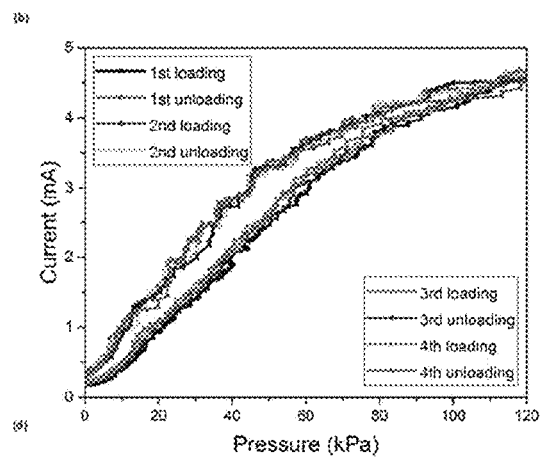
FIG. 7B shows current-pressure plots without capsule (bare sensor)
Figure 7C:
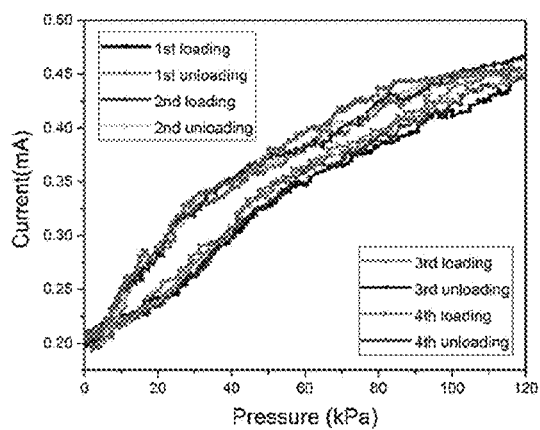
FIG. 7C shows current-pressure plots with capsule.
Figure 7D:
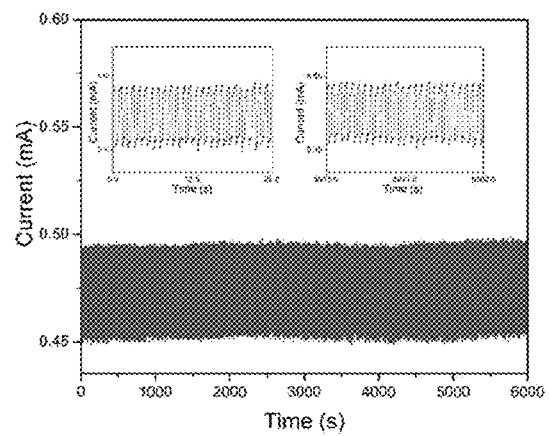
FIG. 7D shows a periodic loading-unloading test over 6000 cycles for the liquid encapsulation device.

FIG. 7B presents the output current-pressure transfer curves of the BP sensors without the liquid encapsulation, and FIG. 7C presents the output current-pressure transfer curves of the BP sensors with the liquid encapsulation. During loading and unloading cycles, both sensors show some hysteresis. The stability of the liquid encapsulation sensor is examined via the periodic loading-unloading input test, where no retention is observed after 6000 cycles. The results of the stability test are shown in FIG. 7D.

The capsule technology in the present disclosure is an encapsulation device that can enhance the performance of all small-scale wearable/flexible devices, e.g., pulse tracker or BP sensor, i.e., to relax the precision alignment requirement without sacrificing the signal quality. Accordingly, the capsule technology in the present disclosure helps true adoption of wearable technologies for personal use.

According the above comparative result, it shows that the liquid encapsulation device and the corresponding fabricating method can achieve a technical solution which substantially relaxes the required alignment precision between the sensor and the target, e.g., blood vessels, and achieves high robustness and enhanced mechanical properties.

Although the preferred examples of the present application have been described, those skilled in the art can make variations or modifications to these examples upon knowing the basic inventive concept. The appended claims are intended to be considered as comprising the preferred examples and all the variations or modifications fell into the scope of the present application.

What is claimed is:

1. A liquid encapsulation device comprising:
    a substrate having an upper surface with a central concave portion;
    a protection piece sealed on the upper surface of the substrate, wherein the protection piece comprises an upper protection layer and a lower protection layer; and
    at least one sensor being used for detecting an epidermal pulse as well as a blood pressure measurement from a blood vessel, the at least one sensor being sandwiched between the upper protection layer and one side of the lower protection layer, the one side facing away from the substrate,
    wherein the central concave portion is filled with liquid and the sensor is arranged above the central concave portion, and
    wherein the substrate, the upper protection layer and the lower protection layer are made of stretchable flexible materials, and
    wherein the liquid in the central concave portion serves as a medium to propagate a pressure wave from the blood vessel to the at least one sensor, to relax a required alignment precision between the at least one sensor and the blood vessel.

2. The device according to claim 1, wherein the sensor is selected from one member of a group consisting of pressure sensor, strain sensor, displacement sensor, and vibration sensor.

3. The device according to claim 1, wherein the substrate and the protection piece are made of same stretchable materials.

4. The device according to claim 1, wherein the substrate and the protection piece are made of different stretchable materials.

5. The device according to claim 1, wherein the substrate and the protection piece are made of silicone and/or rubber.

6. The device according to claim 1, further comprising:
    an adhesive layer for curing the protection piece onto the upper surface of the substrate.

7. The device according to claim 6, wherein the adhesive layer is made of uncured silicone.

8. A wearable device, comprising the liquid encapsulation device of claim 1.

* * * * *